United States Patent
Linz et al.

(10) Patent No.: US 11,518,771 B2
(45) Date of Patent: Dec. 6, 2022

(54) PROCESS FOR MANUFACTURING ALKYL 7-AMINO-5-METHYL-[1,2,5]OXADIAZOLO[3,4-B]PYRIDINE-CARBOXYLATE

(71) Applicant: Boehringer Ingelheim International GmbH, Ingelheim am Rhein (DE)

(72) Inventors: Guenter Linz, Mittelbiberach (DE); Juergen Daeubler, Ummendorf (DE); Michael Pangerl, Waldalgesheim (DE); Rolf Schmid, Baltringen (DE); Sarah Unger, Unlingen (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 76 days.

(21) Appl. No.: 17/326,382

(22) Filed: May 21, 2021

(65) Prior Publication Data

US 2021/0363156 A1 Nov. 25, 2021

(30) Foreign Application Priority Data

May 22, 2020 (EP) .................................... 20176112

(51) Int. Cl.
*C07D 498/04* (2006.01)

(52) U.S. Cl.
CPC .................................. *C07D 498/04* (2013.01)

(58) Field of Classification Search
CPC .................................................. C07D 498/04
See application file for complete search history.

(56) References Cited

U.S. PATENT DOCUMENTS

| | | | |
|---|---|---|---|
| 2008/0275057 A1 | 11/2008 | Kawabe | |
| 2009/2533673 | 10/2009 | merck | |
| 2011/0078154 A1 | 3/2011 | Rickman et al. | |
| 2012/0009560 A1 | 1/2012 | Coupe et al. | |
| 2015/0018547 A1 | 1/2015 | Takakura et al. | |
| 2021/0038603 A1 | 2/2021 | Trieselmann et al. | |
| 2021/0040077 A1 | 2/2021 | Trieselmann et al. | |

FOREIGN PATENT DOCUMENTS

| | | | |
|---|---|---|---|
| WO | 2008152403 | | 6/2008 |
| WO | 2008101017 | | 8/2008 |
| WO | 2008141843 | A1 | 11/2008 |
| WO | 2010007255 | | 1/2010 |
| WO | 2010007251 | | 6/2010 |
| WO | 2010007253 | | 6/2010 |
| WO | 2010070252 | | 6/2010 |
| WO | 2011006497 | | 1/2011 |
| WO | 2011160630 | | 12/2011 |
| WO | 2011160633 | | 12/2011 |
| WO | 2013092703 | | 6/2013 |
| WO | 2004082383 | | 8/2013 |
| WO | 2013125732 | A1 | 8/2013 |
| WO | 2013192388 | | 12/2013 |
| WO | 2014041195 | | 3/2014 |
| WO | 2015073281 | A1 | 5/2015 |
| WO | 2016044467 | | 3/2016 |
| WO | 2016123275 | | 8/2016 |
| WO | 2016168222 | | 10/2016 |
| WO | 2016168225 | | 10/2016 |
| WO | 2017070680 | A1 | 4/2017 |
| WO | 2018024653 | | 2/2018 |
| WO | 201844663 | A1 | 3/2018 |
| WO | 2019149657 | A1 | 8/2019 |
| WO | 2019149658 | A1 | 8/2019 |
| WO | 2019149659 | A1 | 8/2019 |

OTHER PUBLICATIONS

Vasil'ev, Russian Chem Bulletin, International Edition, vol. 50(7), 2001, 1280-1286. (Year: 2001).*
Vydzhak, Russian Journal of General Chemistry, 2020, vol. 90(8), 1439-1446. (Year: 2020).*
International Search Authority and Written opinion, for PCT/EP2017/069274, dated Sep. 15, 2017.
Kuppens, "Elelvated Ration of acylated to unacylated ghrelin in children and yoiung adults with Prader-Willi syndrome", Endocrine, Humana Press, vol. 50, No. 3, 2015, p. 633-642.
Vasil. Russian Chem Bulletin, Reactions of cyanoturazans with [beta]-dicarbonyl compiunds, 2001, vol. 50, p. 1280-1286.
Hirozane, SLAS Discovery, Identification and Characterization of a new series of Ghrelin O-Acyl Transferase Inhibitors, vol. 23, 2018.
Vasil, Mendellev Communications, Effective Synthesis of Funtionalized furazano, 1994, vol. 2, p. 57-58.
Hirozane, Identification and Characterization of a new series of Ghrelin O-Acyl Transferase Inhibitors, SLAS Discoery, 2017.
Haffner, Intensive Lifestyle Intervention or Metformin on Inflammation and Coagulation in Participants with Impaired Glucose Tolerance, The Diabetes Prevention Research Group, vol. 54, 2007.
Cummings, A preprandial rise in plasma ghrelin, Diabetes, vol. 50, 2001.
Druce, Ghrelinincreases foodintake in obese as well as lean subjects, Int J. of Obesity, vol. 29, 2005.
Zhang, Effect of Des0acyl Ghrelinon Adiposity and Glucose Metabolism, Endocrinology, 2008.
Wierup, The ghrelin cell, Regulatory peptides, vol. 107, 2002.
Broglio, Non-Acelated Ghrelin Counteracts the metabolic but not the neuroendocrine response, J. of Endocrine & Metabolism, vol. 80, 2004.
Delparigi, High circulating Ghrelin, J. Of Endocrinology & Metabolism, vol. 12, 2002.
Granata, Acylated and Unacylated Ghrelin promote Proliferation and inhibit Apositis of pancreatic B-cells and Human Islets, Endocrinology, vol. 2, 2007.
Granata, Des-Acyl Ghrelin Fragment and analogues promote survival of pancreatic b-cells, ACS, vol. 55, 2012.
Andrianov, Synthesis and Properties of 4-aminoo-3-cyanofurazan, Chem of heterocyclic Compunds, vol. 30, 1994.

(Continued)

*Primary Examiner* — D Margaret M Seaman
(74) *Attorney, Agent, or Firm* — David L. Kershner

(57) ABSTRACT

This invention relates to a novel process for making alkyl 7-amino-5-methyl-[1,2,5]-oxadiazolo[3,4-b]pyridine-carboxylate.

22 Claims, No Drawings

(56) References Cited

OTHER PUBLICATIONS

Pagoria, Synthesisand Characterization of mutlicyclic oxadiazoles, Chem. of Heterocyclic Compunds, vol. 53, 2017, p. 760-778.
Bohle, Nucelophilic Addition of Hydroxylamine, J. Org Chem, 2000.
Vasil'ev, Effective Synthesis of Functionalized Furazano, Zelinsky Institute of Organix Chem., 1993.
Vasil'ev, Reaction of Cyanofurans, Russian Chem. Bulletin, vol. 50, 2001, p. 1280-1286.
Ichikawa, Central Research Labs, A new Synthesis of Adenine and 4-Aminoimdazole-5-carboxamide, 1965.
International Search Report for PCT/EP2021/063090 dated Jul. 1, 2021.
International Search Report for PCT/EP2021/063088 dated Jul. 1, 2021.

* cited by examiner

PROCESS FOR MANUFACTURING ALKYL 7-AMINO-5-METHYL-[1,2,5] OXADIAZOLO[3,4-B]PYRIDINE-CARBOXYLATE

FIELD OF THE INVENTION

This invention relates to a novel technical scale process for making alkyl 7-amino-5-methyl-[1,2,5]-oxadiazolo[3,4-b]pyridine-carboxylate 4. Alkyl 7-amino-5-methyl-[1,2,5] oxadiazolo[3,4-b]pyridine-carboxylate 4 is a key intermediate for preparing compounds described in WO 2018/024653, WO 2019/149657, WO 2019/149658 and WO 2019/149659.

BACKGROUND OF THE INVENTION

The synthesis of the 4-amino-1,2,5-oxadiazole-3-carbonitrile 3 via the intermediates 6 and 7 was described by T. Ichikawa et al. (J. Heterocycl. Chem. 1965, 253).

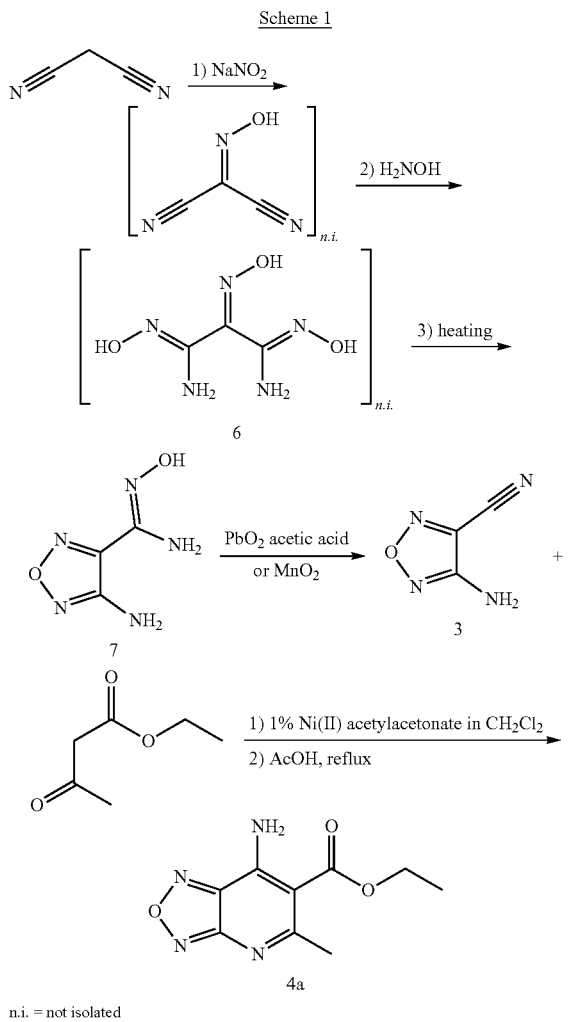

n.i. = not isolated

In 2017, P. F. Pagoria et al. published a modification of Ichikawa's route with improved yield and purity (Chem. Heterocycl. Compounds 2017, 53, 760).

The main drawback of the literature synthesis of 4-amino-1,2,5-oxadiazole-3-carbonitrile 3 is that the intermediate compounds 6 and 7 (as well as compound 3) are highly energetic substances. D. S. Bohle et al. describe that compound 6 "explodes at about 130° C. during DSC experiments, shattering the sample cup" (J. Org. Chem 2000, 65, 1139). Moreover, to induce the cyclization of compound 6 to the oxadiazole 7, the aqueous reaction mixture has to be heated under reflux. This may cause safety issues, particularly in the upscale of this transformation.

Another important drawback of the literature synthesis is the use of lead compounds for the deoximation of oxadiazole 7 to the oxadiazole 3. The use of toxic lead during the preparation of pharmaceuticals is questionable, anyway. However, in the majority of the literature descriptions, the lead is even used in stoichiometric amounts or higher. Thus, the weight load of lead compound in relation to substrate is high. As a result, a lot of toxic lead waste is generated.

As an alternative to the lead containing reagents, WO 2018/44663 describes the use of manganese(IV) oxide as a mild oxidation agent. However, due to the formation of the amide as a side product in significant amounts, the crude product was purified by column chromatography. This is a severe drawback for technical scale, as in large scale, column chromatography is very time-consuming and costly. Moreover, the risk of the highly energetic intermediates will not be overcome by this approach.

A. B. Sheremetev and V. A. Dorokhov et al. showed that ethyl acetoacetate adds to the nitril group of 4-amino-1,2,5-oxadiazole-3-carbonitrile 3 in the presence of catalytic amounts of nickel(II) acetylacetonate in methylene chloride. By adding acetic acid and heating, ethyl 7-amino-5-methyl-[1,2,5]oxadiazolo[3,4-b]pyridine-carboxylate 4a is obtained via intramolecular cyclisation (Mendeleev Communication 1994, 4, 57; Russian Chemical Bulletin, Int. Ed., 2001, 50, 1280).

DETAILED DESCRIPTION OF THE INVENTION

The present invention provides a process for manufacturing alkyl 7-amino-5-methyl-[1,2,5]-oxadiazolo[3,4-b]pyridine-carboxylate 4

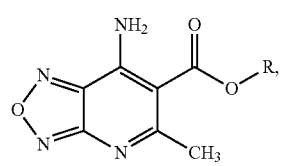

wherein R is $C_{1-3}$-alkyl, comprising (a) reacting malononitrile with sodium nitrite in the presence of a suitable acid, preferably in the presence of hydrobromic acid, in a suitable solvent under slight overpressure;

(b) reacting the reaction mixture obtained by step (a) with a suitable toluenesulfonic acid derivative, preferably with p-toluenesulfonyl chloride, to obtain compound 1;

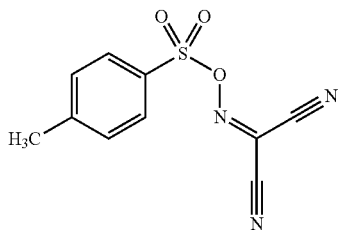

(c) optionally isolating compound 1;
(d) reacting compound 1 in a suitable solvent with hydroxylamine to obtain compound 2;

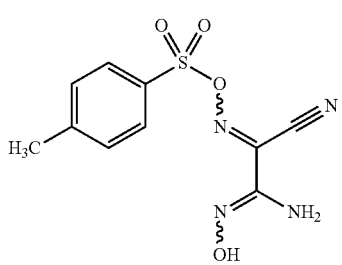

(e) optionally isolating compound 2;
(f) cyclisation of compound 2 in the presence of a base under heating to about 70° C. in a suitable solvent to obtain the oxadiazole 3;

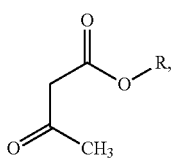

(g) removal of the by-product water formed in step (f) from the reaction mixture by evaporation under reduced pressure;
(h) removal of p-toluenesulfonic acid salt(s) by filtration;
(i) in situ-condensation of compound 3 in the reaction mixture obtained after step (h) with the appropriate beta-keto ester of formula

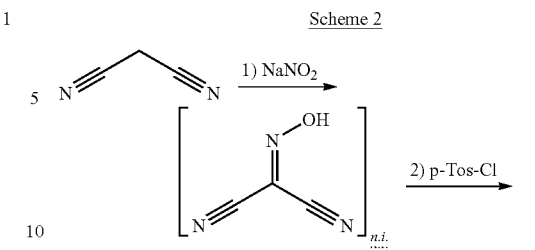

wherein R is $C_{1-3}$-alkyl,
in the presence of a Lewis acid such as zinc dichloride in a suitable solvent; and
(j) isolating compound 4.

In the above process, the beta-keto ester is a $C_{1-3}$-alkyl beta-keto ester. Preferably, the ethyl beta-keto ester is used. Correspondingly, in scheme 2 below, R is $C_{1-3}$-alkyl. Preferably, R is ethyl.

The process according to the invention can be used in technical scale.

Scheme 2

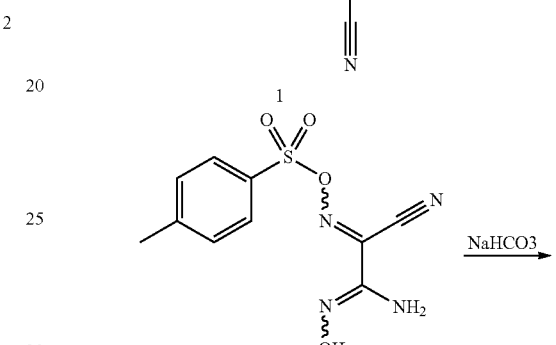

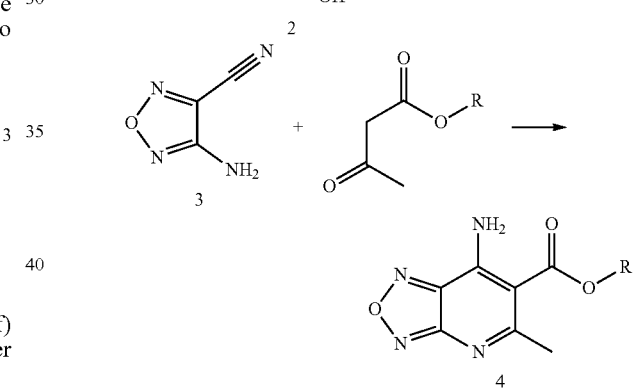

(n.i. = not isolated)

The process according to the present invention overcomes the disadvantages of processes of the prior art by having the distinction of
1) avoiding the highly energetic intermediates 6 and 7,
2) making use of inexpensive and readily accessible starting material and reagents,
3) requiring the isolation of 2 intermediates and the final product, only, all of which can easily be carried out on/in technical scale,
4) yielding alkyl 7-amino-5-methyl-[1,2,5]-oxadiazolo[3,4-b]pyridine-carboxylate 4 in high purity with high overall yield.

Additional advantages of the process according to the invention are as follows:
i) The cyclisation of the intermediate 2 to the oxadiazole 3 can be performed under mild reaction conditions (70° C. for several hours) without the need for an oxidation reagent. This reduces the risks connected with the highly energetic compound 3.

ii) The mild cyclisation conditions became possible due to the use of the tosylate group as a good leaving group that facilitates the intramolecular cyclisation of intermediate 2 to the oxadiazole 3.
iii) The intermediates 1 and 2 are highly crystalline compounds, which simplify isolation and purification.
iv) There is no need for isolation of the highly energetic oxadiazole compound 3 after in situ formation. After partial removal of water and removal of the p-toluenesulfonic acid salt(s), the reaction solution can be further processed in the cyclo-condensation with a suitable beta-keto ester to give the bicyclic oxadiazole compound 4 in good overall yield and purity.

Suitable acids for step (a) include hydrohalic acids like hydrochloric acid and hydrobromic acid, or organic acids like acetic acid. Preferably, hydrobromic acid is used.

A suitable solvent for step (a) is water.

Step (a) is preferably carried out under slight overpressure of up to 0.3 bar at a temperature of 0 to 25° C., preferably at a temperature of 2 to 20° C. The overpressure is caused by the reaction itself due to the formation of nitrogen oxides, and should be maintained up to a certain degree in order to obtain good yields.

Suitable toluenesulfonic acid derivatives useful as reagents for step (b) include p-toluenesulfonic acid anhydride and p-toluensulfonic acid chloride. Preferably, p-toluensulfonic acid chloride is used.

Suitable solvents for step (b) include lipophilic solvents like toluene as well as water, and the mixtures thereof.

Step (b) is preferably carried out at a temperature of 10 to 30° C., more preferably at a temperature of about 20° C.

In step (c), compound 1 is preferably precipitated via addition of an antisolvent like an alcohol such as 2-propanol, and isolated via filtration.

Suitable solvents for step (d) include ethers like tetrahydrofuran and alcohols like 2-propanol as well as water, and the mixtures thereof.

Step (d) is preferably carried out at a temperature of 10 to 30° C., more preferably at a temperature of 20 to 25° C.

In step (e), compound 2 is preferably precipitated via addition of an antisolvent like water and isolated via filtration.

Suitable bases for step (f) include organic bases like triethylamine or inorganic bases like alkali carbonates and alkali hydrogencarbonates. Examples for suitable carbonates are lithium carbonate, sodium carbonate and potassium carbonate. Examples for suitable hydrogencarbonates are lithium hydrogencarbonate, sodium hydrogencarbonate and potassium hydrogencarbonate. Preferably, potassium hydrogencarbonate is used, as the resulting potassium p-toluenesulfonic acid salt has a low solubility in the solvent used and can thus be removed easily via filtration.

Suitable solvents for step (f) include ethers like 1,4-dioxane as well as water, and the mixtures thereof.

Step (f) is preferably carried out at a temperature of 20 to 100° C., more preferably at a temperature of 60 to 80° C.

The appropriate beta-keto ester for step (i) is selected from the group consisting of a $C_{1-3}$-alkyl beta-keto ester. Preferably, the ethyl beta-keto ester is used.

Suitable Lewis acids for step (i) include zinc salts like zinc diacetate or zinc dichloride. Preferably, zinc dichloride is used as Lewis acid.

Suitable solvents for step (i) include an ether like 1,4-dioxane (preferred, if reaction step (i) is carried out in situ) or an alcohol like ethanol (preferred, if an addition isolation step of compound 3 is effected), or the mixtures thereof.

Step (i) is preferably carried out at a temperature of 20 to 100° C., more preferably at a temperature of 60 to 80° C.

In step (j), compound 4 is preferably precipitated via addition of an antisolvent like water and isolated via filtration.

General Definitions

Terms not specifically defined herein should be given the meanings that would be given to them by one of skill in the art in light of the disclosure and context.

In case a compound of the present invention is depicted in form of a chemical name and as a formula, in case of any discrepancy, the formula shall prevail.

Unless specifically indicated, throughout the specification and the appended claims, a given chemical formula or name shall encompass tautomers, rotamers and all stereo, optical and geometrical isomers (e.g. enantiomers, diastereomers, including E/Z isomers) and racemates thereof as well as mixtures in different proportions of the separate enantiomers, mixtures of diastereomers, or mixtures of any of the foregoing forms where such isomers and enantiomers exist, as well solvates thereof such as for instance hydrates.

EXPERIMENTAL SECTION

Note: all intermediates are highly energetic compounds. Special care has to be taken on safety measures.

Example 1

Synthesis of (tosyloxy)carbonimidoyl Dicyanide 1

(Step 1 of the Overall Synthesis)

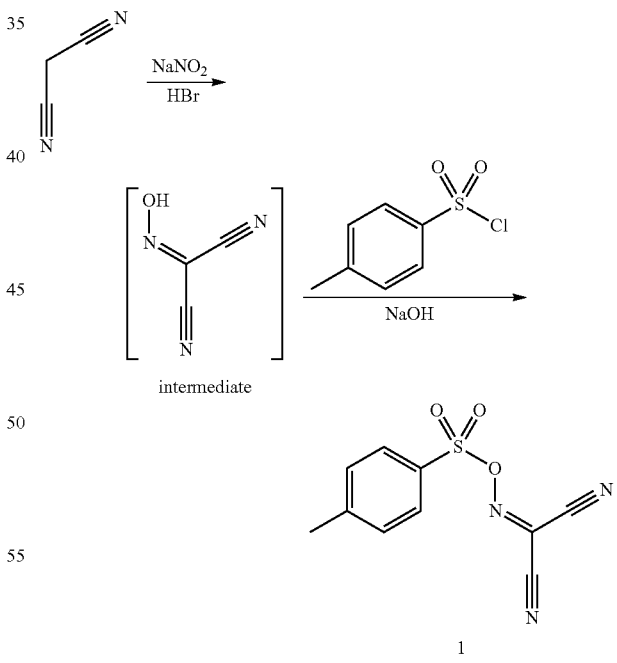

38.3 kg (227.1 mol) hydrobromic acid (48%) and subsequently 7.5 L of purified water (for rinsing) are added to a mixture of 7.5 kg (113.5 mol) malononitrile in 38 L of purified water. At a temperature of 7° C., a solution of 15.7 kg (227.1 mol) sodium nitrite in 26.5 L of purified water are added during 2 hours. The feed tank is rinsed with 3.8 L of purified water and the reaction mixture is stirred for 30 minutes at 7° C. (formation of nitrous gases with a slight overpressure). During 1 hour the temperature is increased to 20° C. and the reaction mixture is stirred at 20° C. till the reaction to the intermediate is complete (control via TLC; reaction is complete in about 30 minutes to 1 hour. The reaction mixture is added to a mixture of 22.7 kg (119.2 mol) p-toluenesulfonyl chloride and 0.63 kg (2.25 mol) tetra-n-butyl-ammonium chloride in 30 L of toluene. The feed tank is rinsed with 7.5 L of purified water. At a temperature of 20° C., a solution of 9.55 kg (119.2 mol) sodium hydroxide (50% in water) in 25 L of purified water is added during 45 minutes. The feed tank is rinsed with 3.5 L of purified water (the pH value should not exceed 4). The reaction mixture is stirred for 18 hours at 20° C. After completion of the reaction (control via TLC), optionally 4 g of seed crystals of 1 (obtained from small scale experiments) and subsequently 30 L 2-propanol are added. The mixture is stirred for 1 hour. The suspension is centrifuged and the filter cake is washed with 15 L of purified water and subsequently, it is washed two times with 15 L of 2-propanol. The product is dried in a vacuum drying cabinet under inertization at 30° C. Yield: 23.1 kg (82% of theory) of 1 as a solid.

$^1$H NMR (400 MHz, CDCl$_3$) δ (ppm)=7.91 (d, 2H), 7.45 (d, 2H), 2.51 (s, 3H)

Example 2

Synthesis of 2-amino-2-(hydroxyimino)-N-(tosyloxy)acetimidoyl Cyanide 2

(Step 2 of the Overall Synthesis)

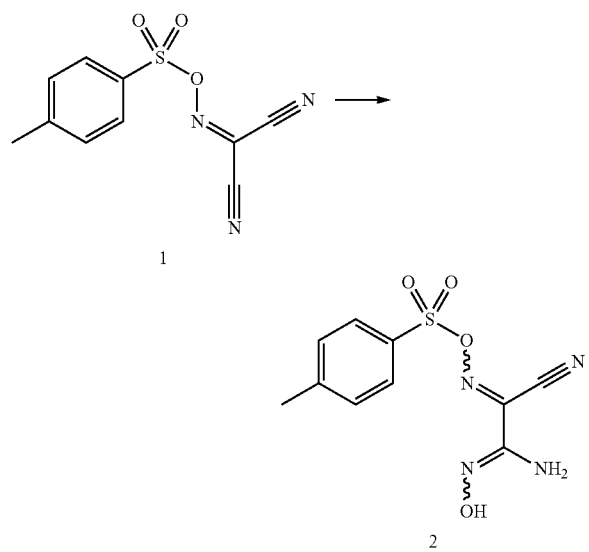

23.49 kg (94.24 mol) 1 are dissolved in 17 L tetrahydrofuran (stabilized) and 47 L 2-propanol. To this solution, a solution of 11.21 kg (127.28 mol) hydroxylamine (37.6 w in water) in 24 L 2-propanol are added in a way, so that the temperature does not exceed 25° C. The feed tank is rinsed with 17 L of 2-propanol. The suspension is stirred for 2 hours at 20° C. After completion of the reaction (control via HPLC), 106 L of purified water are added at 20° C. during 30 minutes. The suspension is stirred for 1 hour at 20° C. The suspension is centrifuged and the filter cake is washed two times with 35 L of 2-propanol. The product is dried in a vacuum drying cabinet at a temperature below 30° C.

Yield: 20.36 kg (76.5% of theory) of 2 as a solid.

$^1$H NMR (400 MHz, DMSO-d6) δ (ppm)=11.7 (s, 1H), 8.05 (d, 2H), 7.53 (d, 2H), 6.13 (bs, 2H), 2.45 (s, 3H)

Example 3

Synthesis of ethyl 7-amino-5-methyl-[1,2,5]-oxadiazolo[3,4-b]pyridine-carboxylate 4

(Steps 3+4 of the Overall Synthesis)

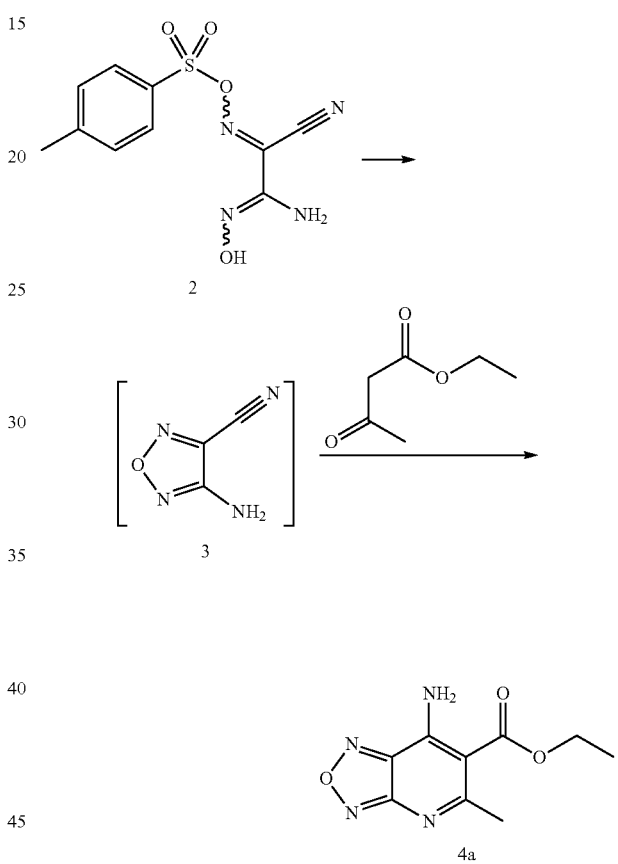

A mixture of 15.25 kg (54.02 mol) 2 and 8.11 kg (81.0 mol) potassium hydrogen carbonate in 152 L 1,4-dioxane and 4.6 L of purified water is stirred at 70° C. After completion of the reaction (control via HPLC; ~8 hours), 45.8 L of solvent are evaporated under reduced pressure. 31 L of 1,4-dioxane are added and 61 L of solvent are evaporated under reduced pressure (removal of water). The suspension is cooled to 20° C. and filtered through a pressure filter into a second reaction vessel which contains a mixture of 7.37 kg (54.07 mol) of zinc dichloride in 15 L of 1,4-dioxane. The first reaction vessel is rinsed with 23 L of 1,4-dioxane and the solvent is filtered through the pressure filter into a second reaction vessel. 7.03 kg (54.02 mol) ethyl acetoacetate are added and the feed tank is rinsed with 8 L of 1,4-dioxane. The reaction mixture is stirred at 70° C. After completion of the reaction (control via HPLC; reaction is complete in about 20 hours), the reaction mixture is cooled to 50° C. and 122 L of purified water are added. The mixture is stirred at 50° C. for 30 minutes. The suspension is cooled to 20° C. and stirred for 30 minutes. The suspension is centrifuged and the filter cake is washed two times with 15 L of purified water. The product is dried in a vacuum drying cabinet under inertization at 40° C.

Yield: 7.71 kg (64.3% of theory) of 4 as a solid.

$^1$H NMR (400 MHz, DMSO-d6) δ (ppm)=8.60 (bs, 2H), 4.35 (q, 2H), 2.60 (s, 3H), 1.32 (t, 3H)

Example 4

Synthesis of 4-amino-1,2,5-oxadiazole-3-carbonitrile 3 (and 5-amino-1,2,4-oxadiazole-3-carbonitrile 5 as Unplanned Side Product)

(Step 3 of the Overall Synthesis)

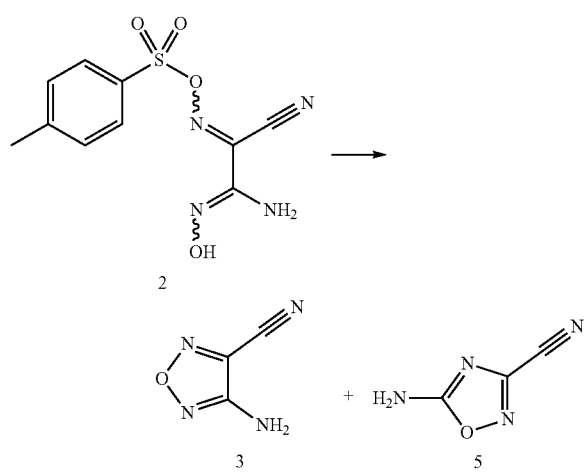

262 mg (3.54 mmol) lithium carbonate is added to a mixture of 1.0 g (3.54 mmol) 2 in 10 mL of 1,4-dioxane and 2 mL of purified water. The reaction mixture is stirred for 5 hours at 60° C. After completion of the reaction (control via HPLC), the reaction mixture is cooled to 20° C. and 10 mL of purified water are added. The aqueous phase is extracted 3 times with toluene. The organic phase is dried over sodium sulfate. After filtration, the solvent is removed under reduced pressure. 260 mg of crude product are obtained as solid.

The crude product is purified via chromatography on silica gel using petrolether/ethylacetate (3:1) als eluent:

Yield: 200 mg (51% of theory) of 3 as a solid.

$^1$H NMR (400 MHz, DMSO-d6) δ (ppm)=7.09 (bs, 2H)

$^{13}$C NMR (100 MHz, DMSO-d6) δ (ppm)=156.9, 126.0, 108.2

$^{15}$N NMR (40 MHz, DMSO-d6) δ (ppm)=−11.9, −334.4

Yield: 22 mg (6% of theory) of 5 as a solid.

$^1$H NMR (400 MHz, DMSO-d6) δ (ppm)=8.67 (bs, 2H)

$^{13}$C NMR (100 MHz, DMSO-d6) δ (ppm)=172.9, 147.3, 109.9

$^{15}$N NMR (40 MHz, DMSO-d6) δ (ppm)=−191.6, −311.6

Example 5

Synthesis of Ethyl 7-amino-5-methyl-[1,2,5]-oxadiazolo[3,4-b]pyridine-carboxylate 4

(Step 4 of the Overall Synthesis)

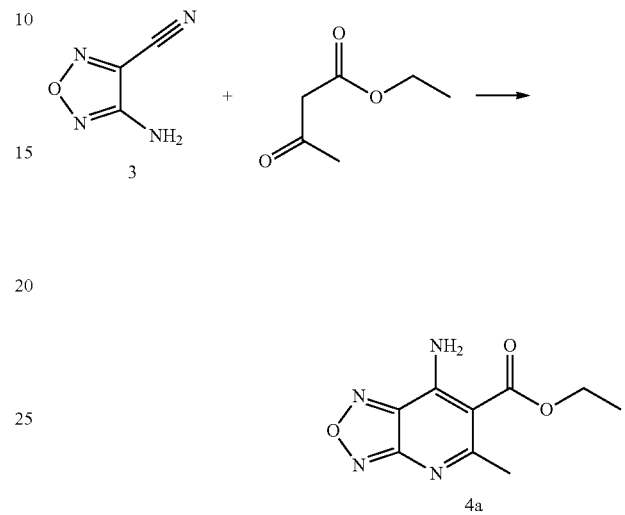

248 g (1.82 mol) zinc dichloride and subsequently 230 mL (1.82 mol) ethyl acetoacetate are added to a suspension of 200 g (1.82 mol) 3 in 1.6 L of ethanol. The reaction mixture is heated under reflux for 15 hours. After completion of the reaction (control via HPLC), the reaction mixture is cooled to 70° C. 1.6 L of purified water are added. The suspension is cooled to 20° C. and stirred for 4 hours. The suspension is suction filtered and the filter cake is washed with 500 mL of ethanol/purified water (1:1). The product is dried in a vacuum drying cabinet at 40° C.

Yield: 334 g (83% of theory) of 4 as a solid.

$^1$H NMR (400 MHz, DMSO-d6) δ (ppm)=8.60 (bs, 2H), 4.35 (q, 2H), 2.60 (s, 3H), 1.32 (t, 3H)

The invention claimed is:

1. A process for making alkyl 7-amino-5-methyl-[1,2,5]-oxadiazolo[3,4-b]pyridine-carboxylate 4

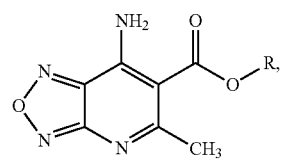

wherein R is $C_{1-3}$-alkyl, comprising
(a) reacting malononitrile with sodium nitrite in the presence of a suitable acid under slight overpressure;
(b) reacting the reaction mixture obtained by step (a) with a suitable toluenesulfonic acid derivative to obtain compound 1;

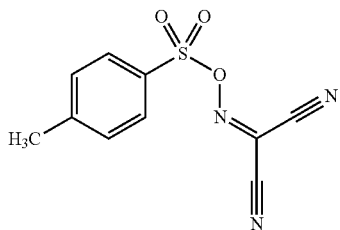

(c) optionally isolating compound 1;
(d) reacting compound 1 in a suitable solvent with hydroxylamine to obtain compound 2;

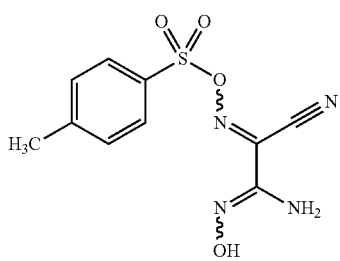

(e) optionally isolating compound 2;
(f) cyclisation of compound 2 in the presence of a base under heating to about 70° C. in a suitable solvent to obtain the oxadiazole 3;

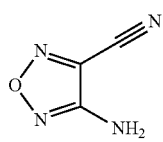

(g) removal of the by-product water formed in step (f) from the reaction mixture by evaporation under reduced pressure;
(h) removal of p-toluensulfonic acid salt(s) by filtration;
(i) in situ-condensation of compound 3 in the reaction mixture obtained after step (h) with the appropriate beta-keto ester of formula

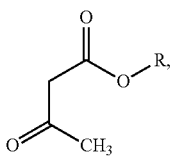

wherein R is $C_{1-3}$-alkyl, in the presence of a Lewis acid in a suitable solvent; and
(j) isolating compound 4.

2. The process according to claim 1 characterized in that isolation step (c) is carried out prior to reaction compound 1 is step (d).

3. The process according to claim 1 characterized in that step (e) is carried out prior to the cyclisation of compound 2 in step (f).

4. The process according to claim 1 characterized in that in step (a), hydrochloric acid, hydrobromic acid or acetic acid is used as the suitable acid and using water as the suitable solvent.

5. The process according to claim 1 characterized in that step (a) is carried out under an overpressure of up to 0.3 bar at a temperature of 0-25° C.

6. The process according to claim 1 characterized in that in step (a), hydrobromic acid is used as the suitable acid; using water as the suitable solvent; and at a temperature of 0-20° C.

7. The process according to claim 1 characterized in that in step (b) the suitable toluenesulfonic acid derivative is toluenesulfonic acid anhydride or toluenesulfonic acid chloride, and the reaction is carried out at a temperature of 10 to 30° C.

8. The process according to claim 1 characterized in that in step (b) the suitable toluenesulfonic acid derivative is toluenesulfonic acid chloride, and the reaction is carried out at a temperature of about 20° C.

9. The process according to claim 1 characterized in that in step (c), compound 1 is precipitated via addition of an antisolvent and then isolated via filtration.

10. The process according to claim 1 characterized in that in step (c), compound 1 is precipitated via addition of an alcohol and then isolated via filtration.

11. The process according to claim 1 characterized in that in step (c), compound 1 is precipitated via addition of 2-propanol and then isolated via filtration.

12. The process according to claim 1 characterized in that in step (d), the reaction is carried out at a temperature of 10 to 30° C. and in a solvent comprising ethers, alcohols, water, or mixtures thereof.

13. The process according to claim 1 characterized in that in step (d), the reaction is carried out at a temperature of 20 to 25° C. and in a solvent comprising tetrahydrofuran, 2-propanol, water, or mixtures.

14. The process according to claim 1 characterized in that in step (e), compound 2 is precipitated via addition of an antisolvent and then isolated via filtration.

15. The process according to claim 1 characterized in that in step (e), compound 2 is precipitated via addition of water and then isolated via filtration.

16. The process according to claim 1 characterized in that in step (f), the cyclisation is carried out in the presence of triethylamine, an alkali carbonate or an alkali hydrogencarbonate; in a solvent comprising ethers, water, or mixtures thereof; and at a temperature of 20 to 100° C.

17. The process according to claim 1 characterized in that in step (f), the alkali carbonate is selected from the group consisting of lithium carbonate, sodium carbonate and potassium carbonate; the alkali hydrogencarbonate is selected from the group consisting of lithium hydrogencarbonate, sodium hydrogencarbonate and potassium hydrogencarbonate; the ether is 1,4-dioxane; and the temperature is 60 to 80° C.

18. The process according to claim 1 characterized in that in step (i), the in situ-condensation is carried out in the presence of a zinc salt as Lewis acid at a temperature of 20 to 100° C., in a solvent selected from an ether, an alcohol, water, or mixtures thereof.

19. The process according to claim 1 characterized in that in step (i), the in situ-condensation is carried out in the presence of zinc dichloride as Lewis acid; at a temperature of 60 to 80° C.; and using 1,4-dioxane as a solvent.

20. The process according to claim 1 characterized in that in step (j), compound 4 is precipitated via addition of an antisolvent and then isolated via filtration.

21. The process according to claim 1 characterized in that in step (j), compound 4 is precipitated via addition of water 5 and then isolated via filtration.

22. The process according to claim 1 wherein R is ethyl.

* * * * *